(12) United States Patent
May et al.

(10) Patent No.: US 7,854,767 B2
(45) Date of Patent: Dec. 21, 2010

(54) SINGLE ENTRY PORTAL IMPLANT

(75) Inventors: Justin J. May, Leesburg, IN (US);
Andrew J. Steiner, Warsaw, IN (US);
Dean M. J. Acker, Warsaw, IN (US)

(73) Assignee: Zimmer, Inc., Warsaw, IN (US)

( * ) Notice: Subject to any disclaimer, the term of this patent is extended or adjusted under 35 U.S.C. 154(b) by 58 days.

(21) Appl. No.: 11/763,825

(22) Filed: Jun. 15, 2007

(65) Prior Publication Data

US 2008/0312749 A1 Dec. 18, 2008

(51) Int. Cl.
*A61F 2/30* (2006.01)
*A61F 2/32* (2006.01)

(52) U.S. Cl. ............... 623/18.11; 623/22.11; 623/22.4; 623/22.42

(58) Field of Classification Search ..... 623/22.4–22.46, 623/23.15, 23.23, 23.26, 23.35, 18.11, 22.11; *A61F 2/30, A61F 2/32*
See application file for complete search history.

(56) References Cited

U.S. PATENT DOCUMENTS

| | | | |
|---|---|---|---|
| 2,785,673 | A | 3/1957 | Anderson |
| 4,795,473 | A | 1/1989 | Grimes |
| 4,955,886 | A * | 9/1990 | Pawluk ............... 606/280 |
| 6,284,002 | B1 | 9/2001 | Sotereanos |
| 6,447,514 | B1 | 9/2002 | Stalcup et al. |
| 6,616,697 | B2 | 9/2003 | Sotereanos |
| 6,949,101 | B2 | 9/2005 | McCleary et al. |
| 7,104,995 | B2 | 9/2006 | Crofford |
| 2002/0111689 | A1 | 8/2002 | Hyde, Jr. |
| 2003/0050704 | A1 | 3/2003 | Keynan |
| 2003/0060889 | A1 | 3/2003 | Tarabishy |
| 2003/0130741 | A1 | 7/2003 | McMinn |
| 2003/0163202 | A1 | 8/2003 | Lakin |
| 2004/0049192 | A1 | 3/2004 | Shimizu |
| 2005/0125067 | A1 * | 6/2005 | Sweeney ............... 623/19.14 |

FOREIGN PATENT DOCUMENTS

| | | |
|---|---|---|
| DE | 8701164 U1 | 6/1987 |
| EP | 1240879 A2 | 9/2002 |
| JP | 2004-154530 | 6/2004 |
| WO | WO01/49193 | 7/2001 |
| WO | WO01/49218 | 7/2001 |
| WO | WO2005/092219 | 10/2005 |
| WO | 2007009123 A2 | 1/2007 |

OTHER PUBLICATIONS

European Search Report mailed Oct. 7, 2008 in related European application No. EP08252035.4.

* cited by examiner

*Primary Examiner*—William H Matthews
*Assistant Examiner*—Jason-Dennis Stewart
(74) *Attorney, Agent, or Firm*—Baker & Daniels LLP

(57) ABSTRACT

A modular prosthesis that may be implanted in a highly minimally invasive manner. Specifically, the modular prosthesis may include a neck and an anchor. Both the neck and the anchor are configured to be inserted and connected together through a lateral aspect of a long bone adjacent to the proximal end of the long bone. In one exemplary embodiment, the neck includes a body having a head end, configured for attachment to another prosthetic component, such as a corresponding articulating component, and an aperture extending therethrough. The anchor may be sized for receipt within the aperture formed in the neck. Additionally, the anchor may be configured such that the anchor engages the walls forming the aperture in the neck to secure the components together.

31 Claims, 9 Drawing Sheets

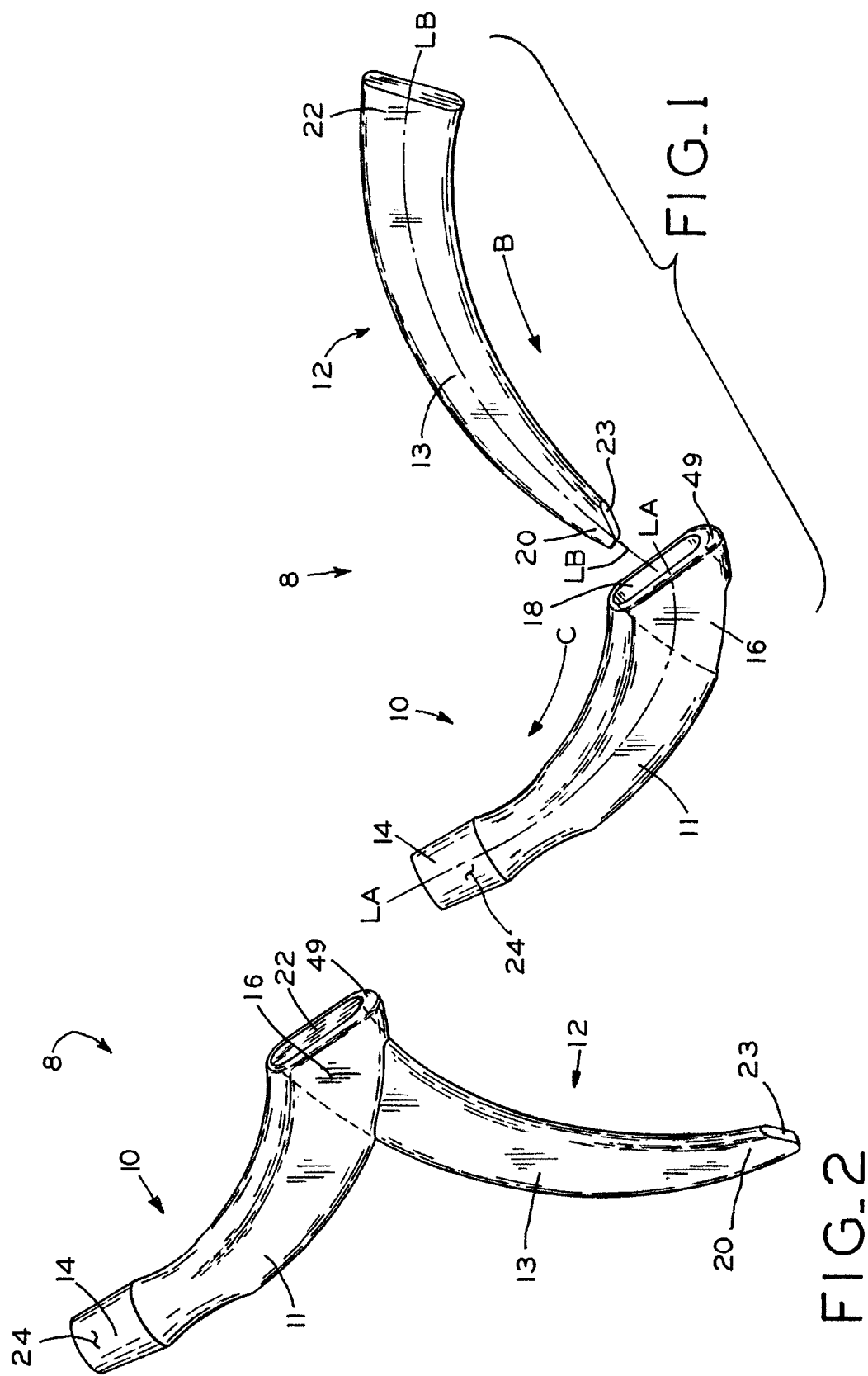

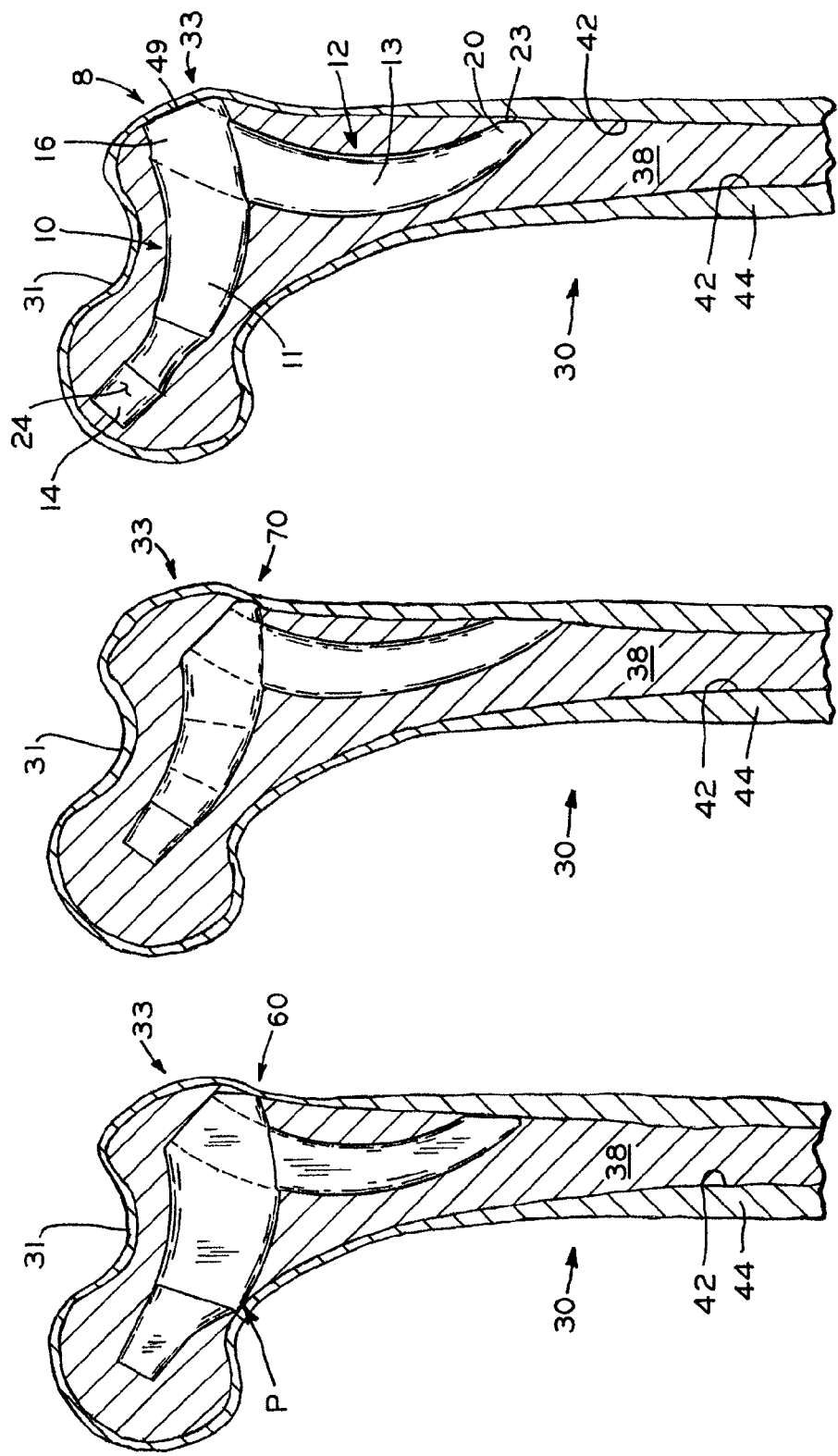

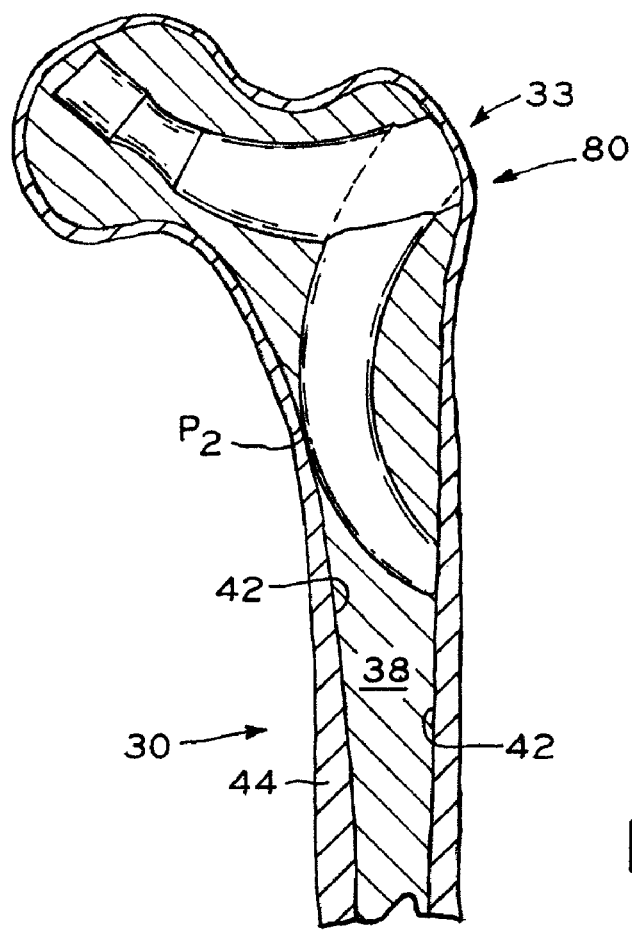
FIG_10
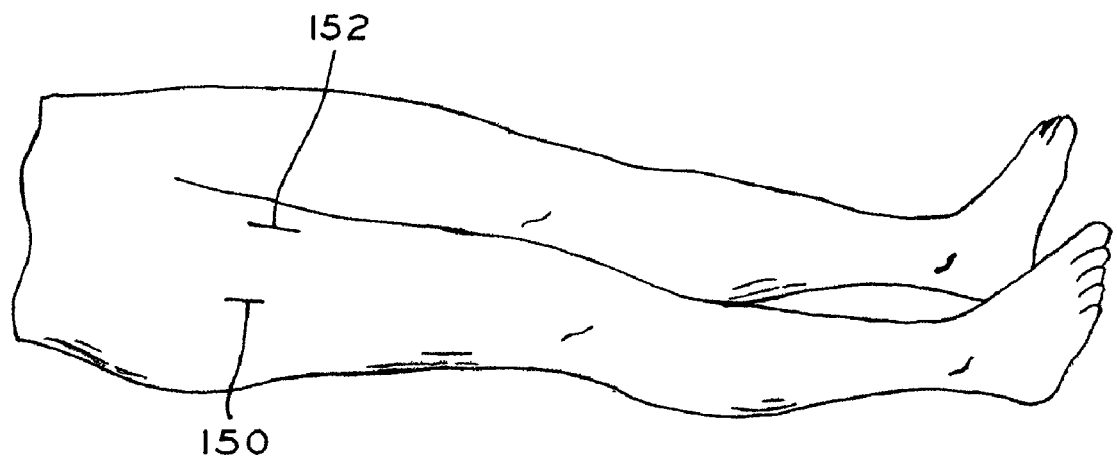
FIG_11

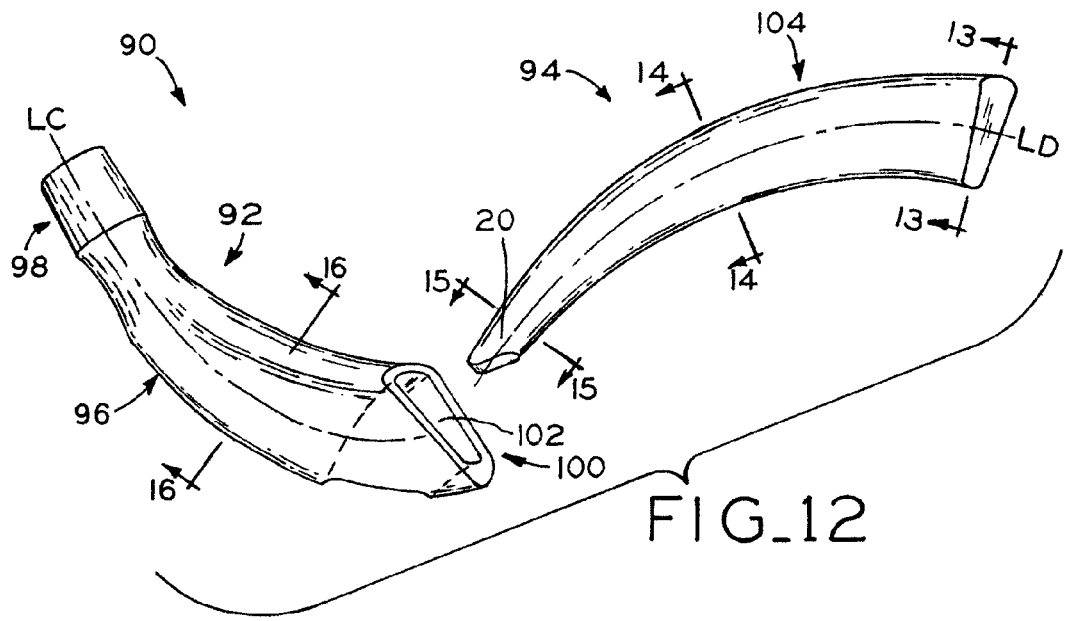
FIG_12
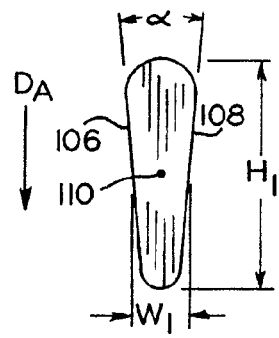
FIG_13
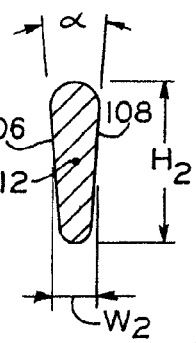
FIG_14
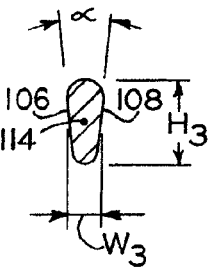
FIG_15
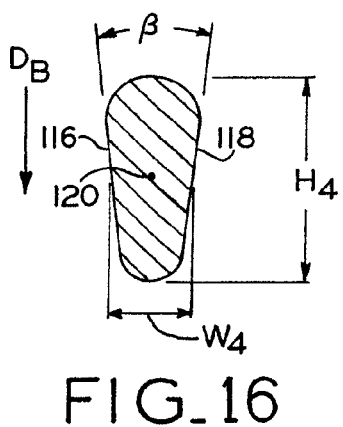
FIG_16

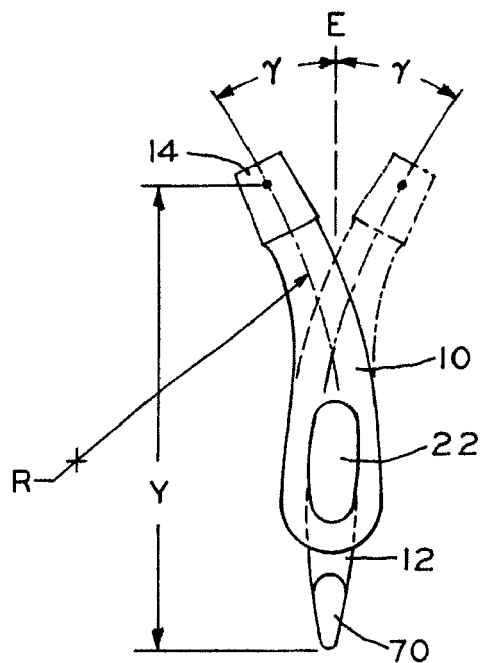
FIG_17
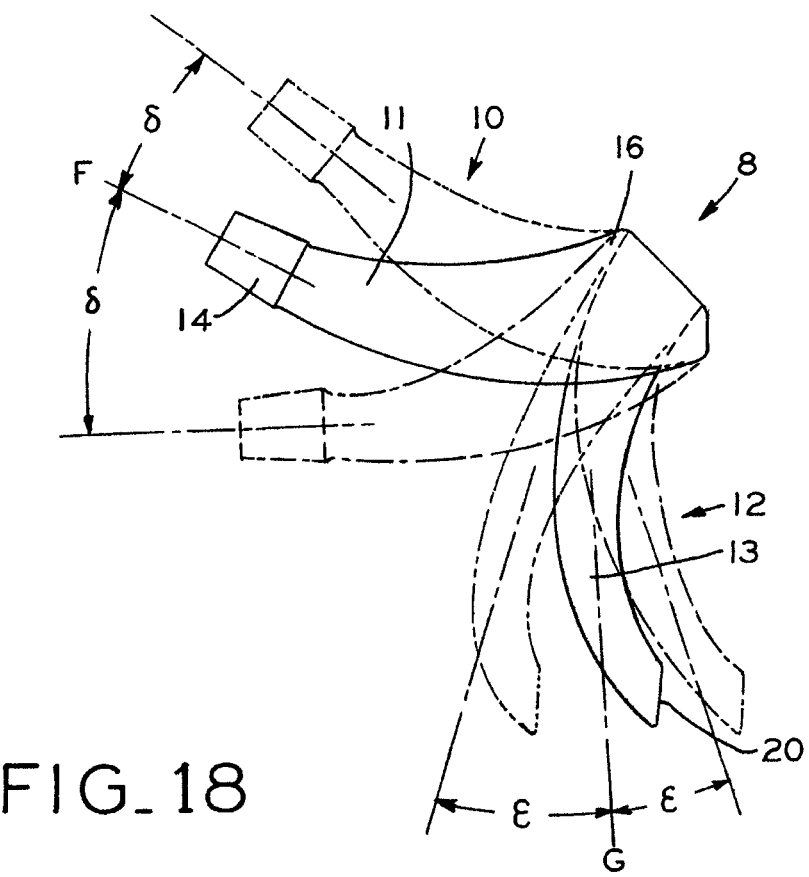
FIG_18

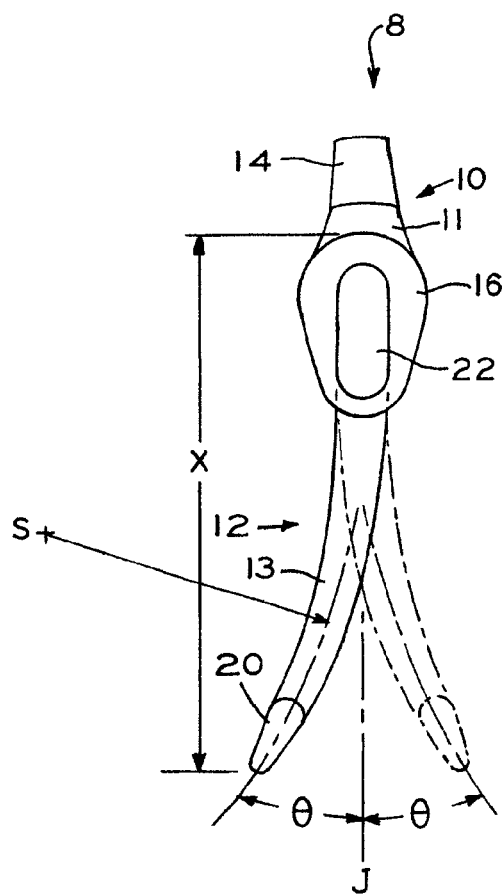
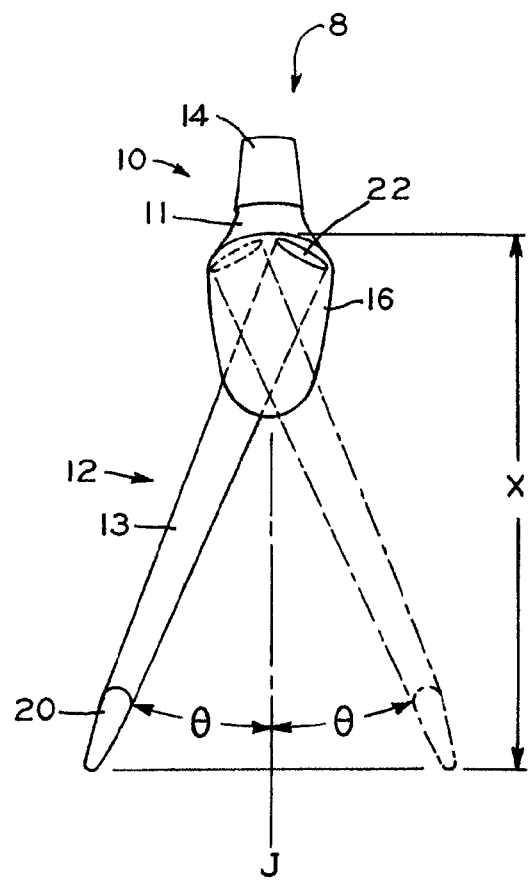
FIG_19  FIG_20

SINGLE ENTRY PORTAL IMPLANT

BACKGROUND

1. Field of the Invention

The present invention relates to a prosthetic system and the surgical methods for utilizing the same.

2. Description of the Related Art

Prostheses are commonly utilized to repair and/or replace damaged bone and tissue in the human body. For example, a hip prosthesis may be implanted to replace damaged or destroyed bone in the femur and/or acetabulum and to recreate the natural, anatomical articulation of the hip joint. To implant a prosthesis, orthopedic surgery is performed which requires the creation of an incision in the skin of the patient and may necessitate the retraction of surrounding tissue to provide a surgeon with access to the surgical site.

To facilitate the implantation of a prosthesis, a modular prosthesis may be utilized. Modular prostheses have several individual, distinct components which are connected together to form the final, implanted prosthesis. For example, a modular femoral prosthesis may include individual stem, neck, and head components which are connected together to form the final, implanted femoral prosthesis. Additionally, any individual component, e.g., the femoral head component in a modular femoral prosthesis, may be selected from several different components having various sizes and configurations, all of which are included in the modular prosthesis system. By selecting the appropriate individual components, the surgeon may assemble a prosthesis that may closely approximate the natural anatomy of the patient.

Additionally, by utilizing modular prostheses, the size of the individual components that are implanted is lessened. As a result, the size of the corresponding incisions necessary to implant the prostheses are also lessened, allowing the surgeon to implant the prostheses using minimally invasive surgical techniques, i.e., surgical techniques that minimize trauma to soft tissue surrounding the surgical site. While utilizing minimally invasive surgical techniques provides a number of benefits, such as lessening the amount of tissue sacrificed and shortening recovery time, currently utilized modular prostheses still require significant exposure of the bone and/or joint in order to provide a surgeon with sufficient access to prepare the bone stock and properly align and size the prostheses.

SUMMARY

The present invention relates to a prosthetic system and the surgical methods for utilizing the same. In one embodiment, the prosthetic system provides a modular prosthesis that may be implanted in a highly minimally invasive manner. Specifically, the modular prosthesis may include a neck and an anchor. Both the neck and the anchor are configured to be inserted and connected together through a lateral aspect of a long bone adjacent to the proximal end of the long bone. In one exemplary embodiment, the neck includes a body having a head end, configured for attachment to another prosthetic component, such as a corresponding articulating component, and an aperture extending therethrough. The anchor may be sized for receipt within the aperture formed in the neck. Additionally, the anchor may be configured such that the anchor engages the walls forming the aperture in the neck to secure the components together. In another exemplary embodiment, an aperture is formed within the anchor. In this embodiment, the neck is sized for receipt within the aperture formed in the anchor.

Advantageously, the modular prosthesis for the present invention may be inserted laterally through a highly minimally invasive incision and into the greater trochanter of the femur, for example, or, if utilized in a shoulder prosthesis, laterally through a highly minimally invasive trans-deltoid incision and into the proximal end of the humerus. By using a highly minimally invasive incision, musculature and ligamentus structures, which are normally sacrificed during modular prosthesis implantation, may be saved. Further, bony structure, which may be sacrificed to create sufficient room for implantation of the prosthesis within the joint itself, may also be preserved. This allows for a patient to retain additional natural bone stock which may provide additional strength and stability to the replaced joint. Additionally, by using highly minimally invasive incisions in conjunction with the modular prosthesis of the present invention, the joint which is replaced is never fully exposed and the capsule surrounding the joint is preserved.

In one form thereof, the present invention provides a modular prosthesis configured for receipt within a portion of a long bone, the modular prosthesis including: a neck including an elongate body having a longitudinal axis, the body sized to extend through the long bone from a lateral aspect of the long bone to a head of the long bone; and an anchor having a longitudinal axis, the anchor sized to extend through the lateral aspect of the long bone and substantially along the anatomical axis of the long bone, wherein one of the neck and the anchor includes an aperture extending therethrough substantially transverse to the respective longitudinal axis and the other of the neck and the anchor is sized for receipt within the aperture.

In another form thereof, the present invention provides a modular prosthesis configured for receipt within a portion of a long bone, the long bone having an articulating head, the modular prosthesis including: a neck including an elongate body having a longitudinal axis and connection means form securing the neck within the long bone, the body sized to extend through the long bone from a lateral aspect of the long bone to a head of the long bone; and anchor means for anchoring said neck to the long bone when the anchor means is engaged with the connection means, the anchor means sized to extend through the lateral aspect of the long bone and into an intramedullary canal of the long bone.

In yet another form thereof, the present invention provides a method for replacing the head of a long bone including the steps of: osteotomizing the head of the long bone; inserting a neck having a longitudinal axis through a long bone, the neck extending from a lateral aspect of the long bone to a position occupied by the head of the long bone before the head of the long bone was osteotomized from the long bone; inserting an anchor into a long bone through the lateral aspect of the long bone in a direction transverse to the longitudinal axis of the neck; and securing the anchor to the neck.

In yet another form thereof, the present invention provides a method for replacing the head of a long bone including the steps of: osteotomizing the head of a long bone; forming a highly minimally invasive lateral incision; inserting a neck having a longitudinal axis through the lateral incision and into a long bone, the neck extending from a lateral aspect of the long bone to a position occupied by the head of the long bone before the head of the long bone was osteotomized from the long bone; inserting an anchor into a long bone through the lateral incision and into a lateral aspect of the long bone in a direction transverse to the longitudinal axis of the neck; and securing the anchor to the neck.

BRIEF DESCRIPTION OF THE DRAWINGS

The above-mentioned and other features and advantages of this invention, and the manner of attaining them, will become more apparent and the invention itself will be better understood by reference to the following description of embodiments of the invention taken in conjunction with the accompanying drawings, wherein:

FIG. 1 is an exploded perspective view of the modular prosthesis of the present invention;

FIG. 2 is a perspective view of the modular prosthesis of FIG. 1;

FIG. 7 is a cross-sectional view of a femur showing a modular prosthesis according to one embodiment of the present invention;

FIG. 8 is a cross-sectional view of a femur and a modular prosthesis according to another embodiment of the present invention superimposed thereon;

FIG. 9 is a cross-sectional view of a femur showing the modular prosthesis of FIG. 1 superimposed thereon;

FIG. 10 is a cross-section view of a femur showing a modular prosthesis according to another embodiment of the present invention superimposed thereon;

FIG. 11 is a fragmentary perspective view of a human body, depicting at least one highly minimally invasive incision;

FIG. 12 is an exploded perspective view of a modular prosthesis according to another embodiment of the present invention;

FIG. 13 is a cross-sectional view of a component of the modular prosthesis of FIG. 12 taken along line 13-13 of FIG. 12;

FIG. 14 is a cross-sectional view of a component of the modular prosthesis of FIG. 12 taken along line 14-14 of FIG. 12;

FIG. 15 is a cross-sectional view of a component of the modular prosthesis of FIG. 12 taken along line 15-15 of FIG. 12;

FIG. 16 is a cross-sectional view of a component of the modular prosthesis of FIG. 12 taken along line 16-16 of FIG. 12;

FIG. 17 is a plan view of a modular prosthesis depicting an alternative geometry;

FIG. 18 is a side view of a modular prosthesis depicting another alternative geometry;

FIG. 19 is a lateral view of a modular prosthesis depicting another alternative geometry;

FIG. 20 is a lateral view of a modular prosthesis depicting another alternative geometry;

Corresponding reference characters indicate corresponding parts throughout the several views. The exemplifications set out herein illustrate preferred embodiments of the invention and such exemplifications are not to be construed as limiting the scope of the invention in any manner.

DETAILED DESCRIPTION

Figures 3, 4:
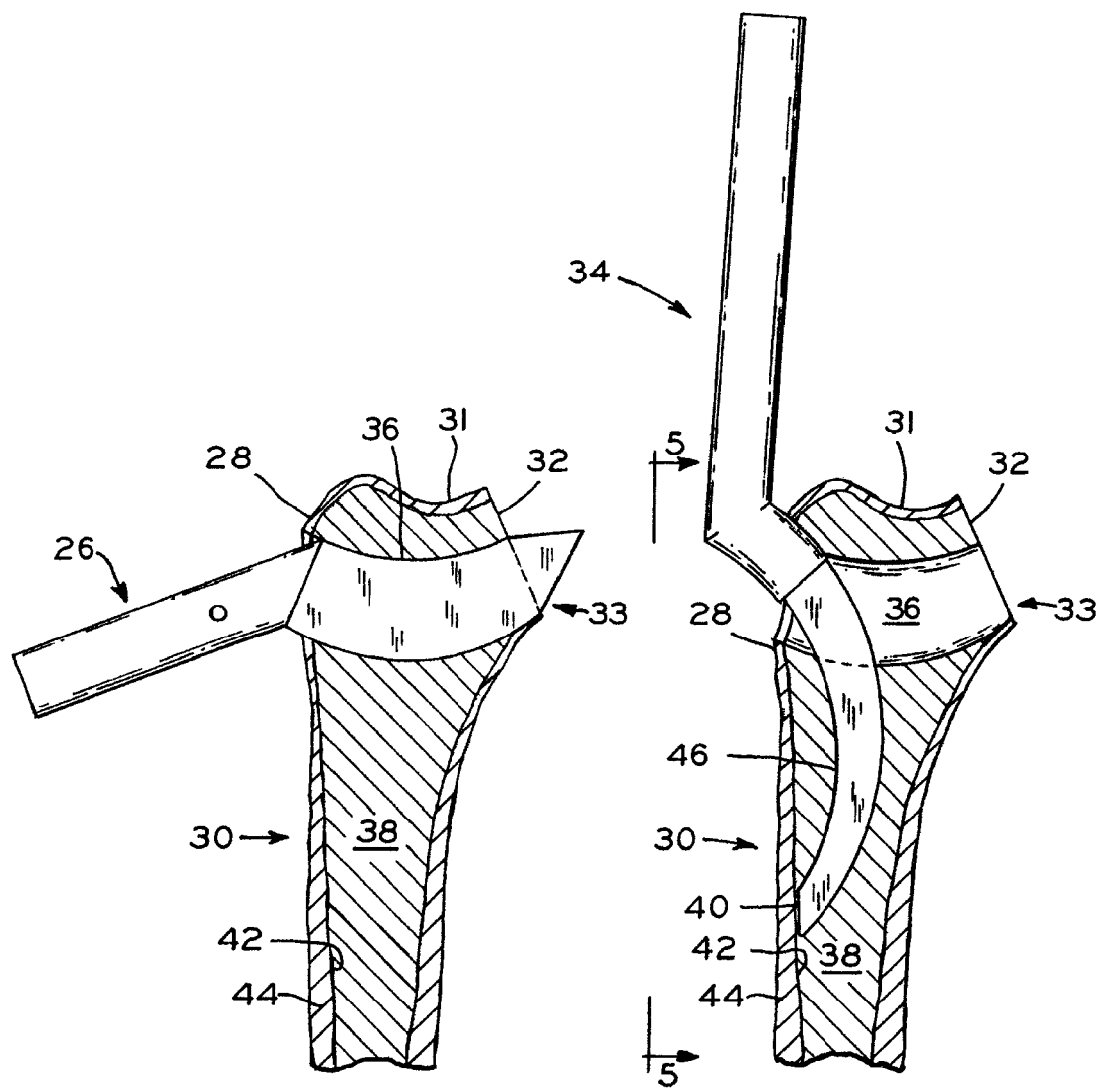
FIG. 3 is a cross-sectional view of a femur including a rasp utilized in preparation of the femur.
FIG. 4 is a cross-sectional view of the femur including a second rasp utilized in the preparation of the femur.

Referring to FIG. 1, modular prosthesis 8 is depicted including neck 10 and anchor 12. Neck 10 includes body 11 having head end 14 and connection end 16. Body 11 also defines curved longitudinal axis LA extending therethrough. Connection end 16 of body 11 includes aperture 18 sized to receive anchor 12. While described and depicted herein as formed in neck 10, aperture 18 may be formed in anchor 12 and the components, i.e., neck 10 and anchor 12, may be connected in a manner substantially similar to that described in detail below. Anchor 12 includes body 13 that defines curved longitudinal axis LB. In one exemplary embodiment, the walls of neck 10 defining aperture 18 are tapered to mate with the corresponding tapered geometry of seating end 22 of anchor 12. In this embodiment, to assemble neck 10 and anchor 12, bone connecting end 20 of anchor 12 is inserted through aperture 18 of neck 10. As anchor 12 is advanced through aperture 18, seating end 22 of anchor 12 matingly engages the wall defining aperture 18 of neck 10 to form a taper lock. This interaction prevents further advancement of anchor 12 through aperture 18 of neck 10 and secures anchor 12 to neck 10. Referring to FIG. 2, modular prosthesis 8 is shown with anchor 12 securely seated within aperture 18 of neck 10. While described and depicted herein as having a tapered geometry, aperture 18 of neck 10 and seating end 22 of anchor 12 may have any complementary geometry capable of securing the components together. Additionally, in another exemplary embodiment, the securement of anchor 12 to neck 10 is provided by a separate component, such as a fastener.

As described and depicted herein, the cross-section of body 11 of neck 10 and body 13 of anchor 12, respectively, are both oval. However, the cross-sections of bodies 11, 13 may have any geometry, such as those described below with reference to FIGS. 7-10 and 12-20. For example, the cross-sections of bodies 11, 13 may be circular or may have a complex compound curvature. By selecting the appropriate cross-sectional geometry for a particular application, load transfer benefits that increase the useful life of modular prosthesis 8 may be provided. Additionally, the geometry of bodies 11, 13 along longitudinal axes LA, LB, respectively, may be altered. For example, in one exemplary embodiment, longitudinal axis LA of body 11 of neck 10 has an anatomical curvature. In this embodiment, the anatomical curvature of body 11 substantially mimics the curvature of proximal end 31 of neck 33 of femur 30, as shown in FIG. 9, for example. By varying the geometry of bodies 11, 13 to match the appropriate anatomical structures, e.g., the profile of the long bone into which bodies 11, 13 are to be implanted, additional musculature and ligamentus structures may be preserved. While described and depicted herein with specific reference to femur 30, modular prosthesis 8 may be use in conjunction with any long bone, such as the humerus, and may include an anatomical curvature substantially similar to the specific anatomical geometry of any long bone.

Referring to FIG. 9, which shows the geometry of modular prosthesis 8 relative to femur 30, the tapered curvature of bodies 11, 13 of neck 10 and anchor 12 may be formed by varying the radii of bodies 11, 13 along longitudinal axes LA, LB, respectively. Specifically, with reference to FIG. 1 and body 13 of anchor 12, the radius of curvature of body 13 may decrease along longitudinal axis LB in the direction of arrow B. Similarly, the radius of curvature of body 11 of neck 10 may decrease along longitudinal axis LA in the direction of arrow C. In another exemplary embodiment, shown in silhouette in FIG. 6, the radius of bodies 54, 56 of neck 50 and anchor 52, respectively, of modular prosthesis 48 remain substantially constant along longitudinal axes LA, LB, respectively. In this embodiment, the radius of curvature of bodies 54, 56 of neck 50 and anchor 52 may be as low as approximately 2.20, 2.30, or 2.40 inches or as high as 2.55, 2.65, or 2.75 inches for example. In one exemplary embodiment, the radius of curvature of body 56 of anchor 52 is substantially equal to 2.50 inches. Additionally, as shown in FIGS. 7, 8, 10, other exemplary embodiments of modular prosthesis 8 are depicted as modular prosthesis 60, 70, 80, 90. FIGS. 7-10 depict femur 30 having a head, i.e., before the head is osteotomized, to further illustrate the various sizes and designs of modular prosthesis 8, 60, 70, 80.

Referring to FIG. 12, another exemplary embodiment of the modular prosthesis of the present invention is depicted as modular prosthesis 90. Modular prosthesis 90 includes several features that are identical or substantially identical to corresponding features of modular prosthesis 8 and identical reference numerals have been used to identify identical or substantially identical features therebetween. Modular prosthesis 90 includes neck 92 and anchor 94. Similar to modular prosthesis 8 of FIG. 1, neck 92 includes body 96 having head end 98 and connection end 100. Connection end 100 of body 96 includes aperture 102 sized to receive anchor 94. Anchor 94 includes body 104 having curved longitudinal axis LD. While described and depicted herein as formed in neck 92, aperture 102 may be formed in anchor 94 and the components, i.e., neck 92 and anchor 94, may be connected in a manner substantially similar to that described in detail above with respect to modular prosthesis 8.

Referring to FIGS. 13-15, cross-sections of anchor 94 of FIG. 12 are shown, which, in combination, depict the progressive taper design of anchor 94 along longitudinal axis LD. Specifically, referring to FIG. 13, sides 106, 108 of anchor 94 have a first taper in the direction of arrow $D_A$, forming angle α between sides 106, 108. In one exemplary embodiment, angle α is as low as 5, 7, or 10 degrees or as high as 15, 20, or 25 degrees. In another exemplary embodiment, angle α is 15 degrees. In another exemplary embodiment, angle α is 11 degrees. Advantageously, angle α facilitates the seating of anchor 94 within a long bone by creating a wedging action that helps to retain anchor 94 in place. Specifically, by reaming the bone to match the contour of anchor 94, the upper portion of anchor 94, i.e., the portion having the greatest width, is restricted from inferior migration further into the bone and/or from varus migration due to the smaller width of the lower portion of anchor 94.

As shown in FIG. 13, the cross-section of anchor 94 taken along line 13-13 of FIG. 12 has a height $H_1$. In one exemplary embodiment, height $H_1$ may be as low as 0.3, 0.4, or 0.5 inches and as high as 0.6, 0.8, or 1.0 inches. In another exemplary embodiment, height $H_1$ is substantially equal to 0.7 inches. Further, the cross-section of anchor 94 taken along line 13-13 of FIG. 12 has a width $W_1$ taken at midpoint 110 on longitudinal axis LD. In one exemplary embodiment, width $W_1$ may be as low as 0.1, 0.2, or 0.3 inches and as high as 0.4, 0.5, or 0.7 inches. In another exemplary embodiment, width $W_1$ is substantially equal to 0.3 inches. As body 104 of anchor 94 progresses along longitudinal axis LD toward bone contacting end 20, the height and width of body 104 decrease.

Specifically, as shown in FIG. 14, the cross-section of anchor 94 taken along line 14-14 of FIG. 12 has a height $H_2$ and a width $W_2$ taken at midpoint 112 on longitudinal axis LD, with height $H_2$ and width $W_2$ being less than height $H_1$ and width $W_1$, respectively, shown in FIG. 13. In one exemplary embodiment, height $H_2$ may be as low as 0.2, 0.3, or 0.4 inches and as high as 0.5, 0.7, or 0.8 inches. In another exemplary embodiment, height $H_2$ is substantially equal to 0.6 inches. Further, in one exemplary embodiment, width $W_1$ may be as low as 0.05, 0.1, or 0.15 inches and as high as 0.2, 0.3, or 0.5 inches. In another exemplary embodiment, width $W_1$ is substantially equal to 0.18 inches. Referring to FIG. 15, the cross-section of anchor 94 taken along line 15-15 of FIG. 12 has a height $H_3$ and a width $W_3$ taken at midpoint 114 on longitudinal axis LD, with height $H_3$ and width $W_3$ being less than heights $H_1$, $H_2$ and widths $W_1$, $W_2$, respectively, of FIGS. 12 and 13. As a result of the decrease in the height of body 104 of anchor 94 along longitudinal axis LD in the direction of bone contacting end 20, another second taper is formed. Additionally, as a result of the decrease in the width of body 104 of anchor 94 along longitudinal axis LD in the direction of bone contacting end 20, a third taper is formed.

Similar to the taper formed by angle α and discussed in detail above, the second and third tapers of body 104 of anchor 94, i.e., the tapers form by the decreasing height and width, respectively, of body 104, further facilitate the seating of anchor 94 within a long bone by creating a wedging action that helps to retain anchor 94 in place. Specifically, by reaming the bone to match the contour of anchor 94, the portion of anchor 94 opposite bone contacting end 20 is restricted from migrating further into the bone due to the smaller height and width of body 104 of anchor 94 at bone contacting end 20. Additionally, while anchor 94 is described and depicted herein as having three distinct tapers, anchor 94 may utilize any of the tapers described herein individually or in any combination.

Referring to FIG. 16, a cross-section of neck 92 is shown taken along line 16-16 of FIG. 12. Sides 116, 118 of neck 92 have a first taper in the direction of arrow $D_B$, forming angle β therebetween. In one exemplary embodiment, angle β is as low as 5, 7, or 10 degrees or as high as 15, 20, or 25 degrees. In another exemplary embodiment, angle β is 15 degrees. In another exemplary embodiment, angle β is 11 degrees. Advantageously, angle β facilitates the seating of neck 92 within a long bone by creating a wedging action that helps to retain neck 92 in place. Specifically, by reaming the bone to match the contour of neck 92, including the upper portion of neck 92, i.e., the portion having the greatest width, the ability for neck 92 to undergo yarns migration during anatomical loading is restricted due to the smaller width at the lower portion of neck 92. Additionally, as shown in FIG. 16, the cross-section of neck 92 taken along line 16-16 of FIG. 12 includes height $H_4$ and width $W_4$ taken at midpoint 120 on curved longitudinal axis LC. Similar to anchor 94, the height and width of body 96 of neck 92 may decrease along longitudinal axis LC from connection end 100 to head end 98 to form additional tapers. For example, the height of neck 92 at connection end 100 may be substantially equal to 1.0 inch, which may be greater than height $H_4$. Additionally, the height of neck 92 at head end 98 may be substantially equal to 0.875 inches, which may be less than height $H_4$. The formation of additional tapers in body 96 of neck 92 further facilitates the seating of neck 92 within a long bone in a manner substantially similar to the manner described in detail above with respect to anchor 94. Additionally, while neck 92 is described herein as having three distinct tapers, neck 92 may utilize any of the tapers described herein individually or in any combination.

Referring to FIG. 17, another exemplary embodiment of modular prosthesis 8 is shown in which neck 10 has a radius of curvature R in an anterior/posterior direction. Anatomical directions, as used herein, refer to a modular prosthesis, such as modular prosthesis 8, or a component thereof, such as neck 10 and/or anchor 12, in their implanted position. For example, FIG. 17 shows a proximal plan view of modular prosthesis 8. In this proximal plan view a radius of curvature of neck 10 in an anterior/posterior direction can be seen. As a result, head end 14 of neck 10 is anteriorly/posteriorly offset with respect to connection end 16 of neck 10 and body 13 of anchor 12. Specifically, head end 14 of neck 10 may be offset in one of an anterior and a posterior direction by angle γ from central plane E. In certain embodiments, central plane E will correspond to a coronal plane. Additionally, by offsetting head end 14 in one of an anterior and a posterior direction, the overall depth Y of modular prosthesis 8 is lessened. Advantageously, by modifying necks 10 of modular prosthesis 8 to have different anterior/posterior offsets, one of the variety of necks 10 may be selected to form modular prosthesis 8 that best approximates a patient's natural anatomy.

In another exemplary embodiment of modular prosthesis 8, shown in FIG. 18, the position of aperture 18 (FIG. 1) of neck 10 of modular prosthesis 8 may be altered to move body 11 of neck 10 proximally/distally. For example, as shown in solid lines in FIG. 18, neck 10 is in a centered position. By altering the trajectory of aperture 18 as it extends through body 11 of neck 10, as described above, neck 10 may be moved proximally/distally, as shown in dashed lines in FIG. 18, to provide proximal/distal variation to neck 10. Specifically, head end 14 of neck 10 may be angled in one of a proximal and a distal direction by angle δ from central plane F. In another exemplary embodiment, the radius of curvature of body 11 of neck 10 is varied in a proximal/distal direction, while maintaining the trajectory of aperture 18, to position head end 14 of neck 10 in an altered proximal/distal position. In another exemplary embodiment, connection end 16 of neck 10 has a first, fixed radius of curvature in the proximal/distal direction, allowing the position of aperture 18 to be maintained, and the remainder of body 11 has a second, variable radius of curvature in the proximal/distal direction. By varying the second radius of curvature of body 11 in the proximal/distal direction, neck 10 may be provided in different configurations having different proximal/distal positions of head end 14, such as those shown in FIG. 18. Advantageously, by modifying neck 10 of modular prosthesis 8 to have proximal/distal variation, modular prosthesis 8 may be provided with a variety of necks 10 having different proximal/distal positions to properly set the varus/valgus angle of neck 10 to substantially match the natural varus/valgus position of the neck of a long bone of a patient.

Referring to FIG. 18, the position and/or trajectory of aperture 18 (FIG. 1) of neck 10 of modular prosthesis 8 may also be altered to move body 13 of anchor 12 medially/laterally. For example, as shown in solid lines in FIG. 18, anchor 12 is in a centered position. By altering the position and/or trajectory of aperture 18 as it extends through body 11 of neck 10, as described above, anchor 12 may be moved medially/laterally, as shown in dashed lines in FIG. 18, to provide medial/lateral variation to anchor 12. Specifically, bone contacting end 20 of anchor 12 may be angled in one of a medial and lateral direction by angle ε from central plane G. In another embodiment, the radius of curvature of body 13 of anchor 12 is varied in a medial/lateral direction to position bone contacting end 20 of anchor 12 in an altered medial/lateral position. In another exemplary embodiment, seating end 22 of anchor 12 has a first, fixed radius of curvature in the medial/lateral direction, allowing for aperture 18 of neck 10 to maintain a standard position for mating with various anchors 12, and the remainder of body 13 has a second, variable radius of curvature in the medial/lateral direction. By varying the second radius of curvature of body 13 in the medial/lateral direction, a variety of anchors 12 may be provided having different medial/lateral positions of bone contacting end 20, such as those shown in FIG. 18. Advantageously, by modifying anchor 12 of modular prosthesis 8 to have medial/lateral variation, modular prosthesis 8 may be provided with a variety of anchors 12 having different medial/lateral positions to properly set the varus/valgus angle of anchor 12 to substantially match the natural varus/valgus offset of a shaft of a long bone of a patient and to maximize the cortical bone contact of body 13, as described in detail above.

In another exemplary embodiment, shown in FIG. 19, anchor 12 of modular prosthesis 8 may be curved along body 13 in an anterior/posterior direction to position anchor 12 in a anterior/posterior offset position. Specifically, bone contacting end 20 of anchor 12 may be offset in one of an anterior and a posterior direction by angle θ from central plane J. For example, body 13 of anchor 12 may have a radius of curvature S that may be varied to correspondingly vary the offset angle. Advantageously, by modifying anchor 12 of modular prosthesis 8 to have an anterior/posterior offset, modular prosthesis 8 may be provided with a variety of anchors 12 having various anterior/posterior offsets to properly set the flexion/extension angle of anchor 12 of modular prosthesis 8. Additionally, by offsetting bone contacting end 20 in one of an anterior and a posterior direction, the overall height X of modular prosthesis 8 is lessened. Alternatively, in another exemplary embodiment, shown in FIG. 19, a substantially similar anterior/posterior offset of anchor 12 may be achieved by altering the orientation of aperture 18 extending through connection end 16 of neck 10.

While some of the various features of the modular prosthesis of the present invention are described and depicted separately herein, a modular prosthesis including a neck and anchor may be created in accordance with the teachings of the present invention that includes any of the designs discussed herein, such as the individual offsets discussed in detail above, either individually or in any potential combination with one another. Additionally, a series of modular components, such as necks 10 and anchors 12, may be created having varying angles γ, δ, ε, θ. By providing multiple components having varying angles γ, δ, ε, θ, individual components may be selected to create an individual prosthesis that closely replicates an individual patient's natural anatomy.

Figure 6:
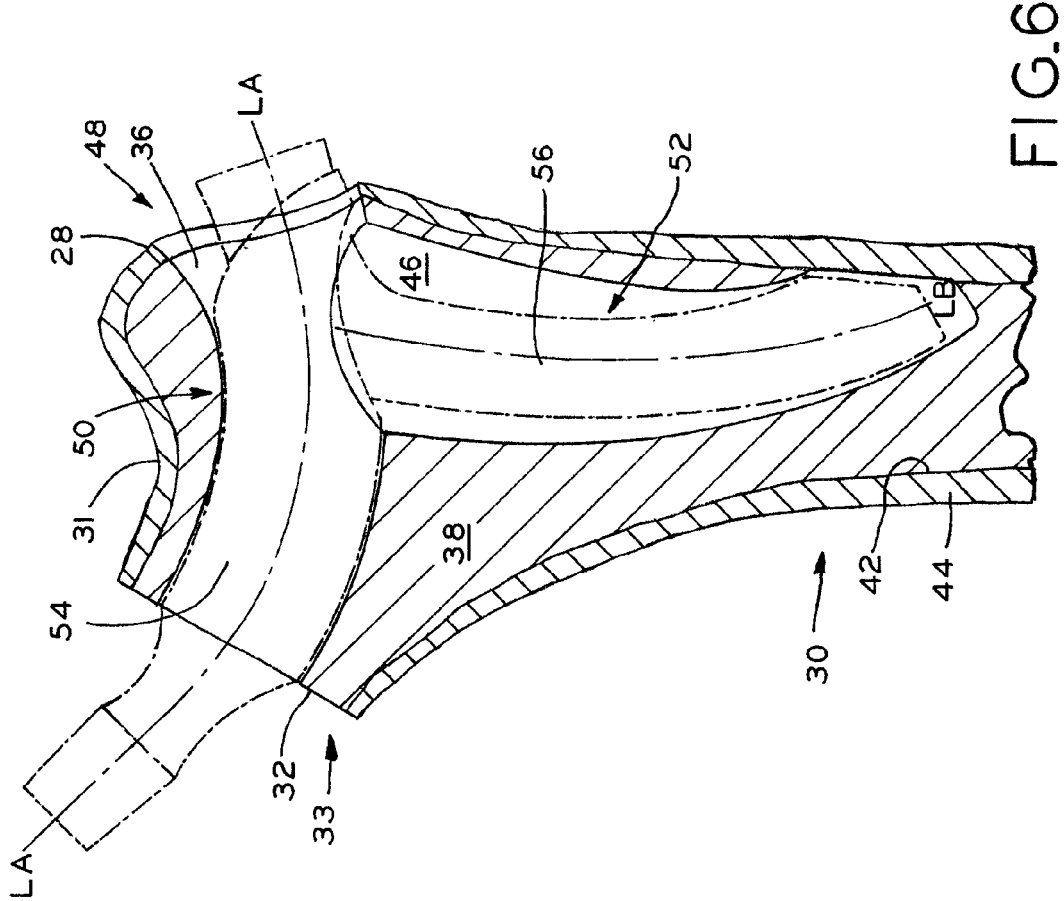
FIG. 6 is a cross-sectional view of the femur of FIG. 5 taken along line 6-6 of FIG. 5.

Irrespective of the modular prosthesis 8, 48, 60, 70, 80, 90 utilized or its respective geometry, each neck of modular prostheses 8, 48, 60, 70, 80, 90 is sized and shaped to extend from a lateral aspect of a long bone to an osteotomized medial portion of the long bone. Specifically, as shown in FIG. 6 with reference to modular prosthesis 48, neck 50 of modular prosthesis 48 extends from lateral aspect 28 of femur 30 to osteotomized surface 32 of femur 30. In this manner, the head end of neck 50 extends from the osteotomized surface 32 of femur 30 to secure a femoral head component (not shown) to modular prosthesis 48, as described in detail below with reference to modular prosthesis 8.

To implant a modular prosthesis of the present invention, such as modular prosthesis 8, a lateral incision is made adjacent the proximal end of a long bone, e.g., femur 30. In addition to the formation of a lateral incision, an anterior incision, such as anterior incision 152 (FIG. 11), may also be formed. In one exemplary embodiment, the lateral incision is made substantially directly adjacent to the greater trochanter of the femur, i.e., at a spot on the epidermis closest to the greater trochanter. In this embodiment, incision 150, shown in FIG. 11, may be highly minimally invasive, i.e., the length of incision 150 may be no greater than two inches. In one exemplary embodiment, the length of incision 150 is less than one and a half inches and, in another exemplary embodiment, is less than one inch. While modular prosthesis 8 may be implanted into any long bone, as discussed above, the implantation of modular prosthesis 8 is described herein with specific reference to femur 30.

Anterior incision 152 is sized to allow for preparation of the acetabulum of the hip joint and for the receipt of an acetabular cup. For example, an acetabular cup such as those disclosed in U.S. Pat. No. 7,044,974, entitled HIP PROSTHESIS WITH A MODULAR ACETABULAR CUP ASSEMBLY, the entire disclosure of which is expressly incorporated by reference herein, may be inserted through anterior incision 152. If utilizing a standard acetabular cup, the size of anterior incision 152 is approximately two to three inches in length. In one exemplary embodiment, the size of anterior incision 152 is less than three inches. The size of anterior incision 152 is limited by the size of the acetabular cup to be implanted. Thus, if a segmental or modular acetabular cup is used, the size of anterior incision 152 may be correspondingly lessened to form a highly minimally invasive incision. In this embodiment, the size of anterior incision 152 is less then two inches.

Referring to FIG. 11, once lateral incision 150 has been made, sequential rasping may be performed to create bore 36 in femur 30. In sequential rasping, a series of progressively larger rasps, ultimately culminating in rasp 26 shown in FIG. 3, are inserted through the lateral incision to form bore 36 extending through lateral aspect 28 of femur 30. Specifically, the smallest diameter rasp is selected from a plurality of rasps and is initially used to create a small bore, substantially smaller than neck 10 of modular prosthesis 8, in femur 30. Once femur 30 has been rasped with the first, smallest diameter rasp and a bore having a size and shape corresponding to the size and shape of the first rasp created, the first rasp is removed and the next largest diameter rasp selected. This rasp is then inserted into the bore created by the first rasp and the process repeated. This procedure is then again repeated until a rasp having a size and shape substantially similar to neck 10, such as rasp 26, can be inserted. Rasp 26 is then used to shape bore 36 of femur 30 to the approximate size and shape of neck 10.

Once rasp 26 has created bore 36 having a geometry substantially similar to that of corresponding neck 10, sequential rasping of bore 46 is performed in same manner as described in detail above with respect to bore 36. In one exemplary embodiment, rasp 26 includes an aperture (not shown) extending therethrough that is substantially similar to aperture 18 of neck 10. In this embodiment, once bore 36 is formed, rasp 26 may be fully inserted into femur 30 and allowed to remain therein. Then, each of series of sequentially larger rasps culminating in rasp 34 may be inserted through the aperture in rasp 26 to guide rasp 34 into the desired alignment for the creation of bore 46. In this manner, the position of each of series of sequentially larger rasps culminating in rasp 34 are referenced by the position of the aperture of rasp 26. Additionally, the sequential rasping of bore 46 is performed through the same portal used for creation of bore 36. By utilizing the same portal, the procedure described herein creates minimal muscular and ligamentus damage, lessening the patient's total recovery time. Once bore 46 has reached a sufficient size to accept rasp 34, shown in FIG. 4 and corresponding in size to anchor 14, rasp 34 is inserted to create the final geometry of bore 46.

As shown in FIG. 4, rasp 34 is inserted along a downward, proximal-distal plane through the lateral portal and bore 36. Rasp 34 is extended through cancellous bone 38 forming the intramedullary canal of femur 30, such that end 40 of rasp 34 contacts inner wall 42 of cortical bone layer 44. Similar to rasp 26, rasp 34 has a geometry that is substantially similar to the geometry of corresponding anchor 12. In one exemplary embodiment, the prosthesis system may include a plurality of rasps 26, 34, which have a geometry substantially congruent with a respective plurality of necks 10 and anchors 12, respectively. In one exemplary embodiment, the plurality of rasps 26, 34 have a geometry that is slightly undersized compared to the respective plurality of necks 10 and anchors 12, respectively. By slightly undersizing rasps 26, 34, necks 10 and anchors 12 are tightly fitted with the surrounding bone once implanted. Thus, a surgeon may select the appropriate rasp 26, 34 for forming bores 36, 46 (FIG. 6) within femur 30 that is appropriate based on the size of the selected neck 10 and anchor 12.

In another exemplary embodiment, bores 36, 46 in femur 30 may be reamed or, alternatively, may be created through sequential reaming, i.e., utilizing reamers of a smaller size and gradually progressing to reamers having a greater size. Additionally, any other method for forming a bore within a long bone, such as drilling, may be used, such as those disclosed in U.S. Pat. No. 6,447,514, entitled POLYMER FILLED HIP FRACTURE FIXATION DEVICE, and U.S. patent application Ser. Nos. 10/155,683, 10/266,319, 10/358,009, 11/061,898, 11/250,927, 11/611,194, each entitled METHOD AND APPARATUS FOR REDUCING FEMORAL FRACTURES, the entire disclosures of which are expressly incorporated by reference herein. Irrespective of the method utilized to create bores 36, 46 in femur 30, rasps 26, 34 may be used to finish bores 36, 46 by creating a final geometry that substantially mimics the geometry of a corresponding neck 10 and anchor 12, respectively, as described in detail above.

Figure 5:
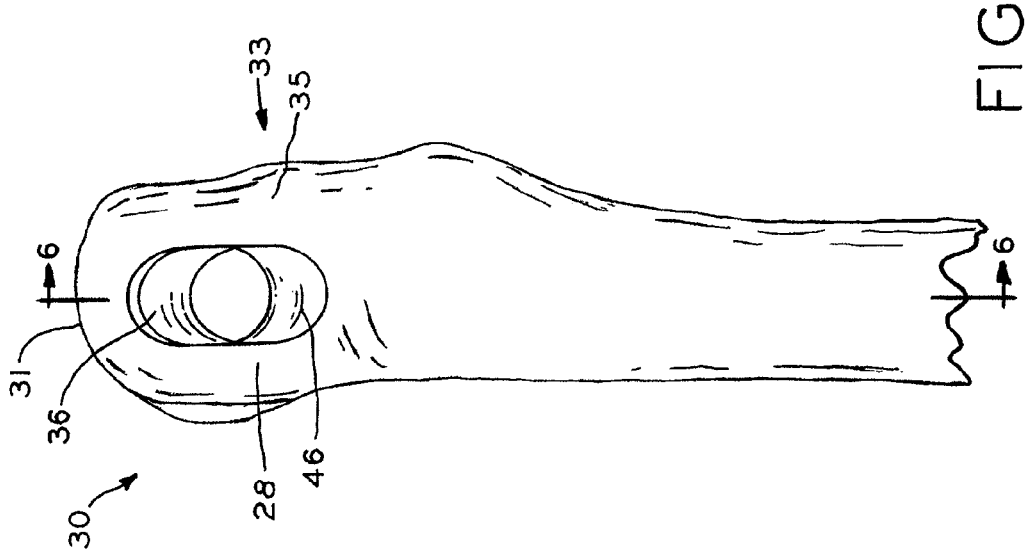
FIG. 5 is a lateral view of the femur of FIG. 4 taken along line 5-5 of FIG. 4.

With bores 36, 46 formed in femur 30, as shown in FIG. 5, modular prosthesis 8 is inserted therein. Specifically, head end 14 of neck 10 is inserted within the lateral portal and bore 36 to extend through femur 30. Specifically, once properly positioned, neck 10 extends from a lateral aspect 28 through osteotomized surface 32 of femur 30. Once neck 10 is properly positioned within bore 36 of femur 30, bone contacting end 20 of anchor 12 is inserted through aperture 18 of neck 10. As anchor 12 is advanced through aperture 18, bone contacting end 20 may contact inner wall 42 of cortical bone layer 44. Specifically, in one exemplary embodiment shown in FIGS. 1, 2, and 9, bone contacting end 20 of anchor 12 includes wall 23 configured to maximize contact with inner wall 42 of cortical bone layer 44. In one exemplary embodiment, wall 23 has an arcuate shape configured to substantially match the arcuate shape of inner wall 42. Once anchor 12 is inserted within aperture 18 of neck 10, anchor 12 prevents removal of neck 10 from femur 30.

Additionally, as shown in FIGS. 7-10, the ends of each respective neck of modular prostheses 8, 60, 70, 80, 90, such as end 49 of neck 10, shown in FIG. 6, also contacts cortical bone layer 44. In this manner, two points of contact between the modular prosthesis and cortical bone layer 44 are established. As shown in FIG. 7, an additional point of contact $P_1$ between cortical bone layer 44 and prosthesis 60 may be established near the head end of the neck. Additionally, as shown in FIG. 10, another point of contact $P_2$ between cortical bone layer 44 and prosthesis 80 may be established along the shaft of femur 30. In one exemplary embodiment, the components of modular prostheses 8, 60, 70, 80, 90 may be interchangeable to provide the customized geometrical configurations that facilitate contact with the cortical bone of the individual patient.

In one exemplary embodiment, the bone contact surfaces and/or the respective necks and anchors of modular prosthesis 8, 60, 70, 80, 90 are coated with or may be formed from a bone ingrowth material, such as a material made using Trabecular Metal Technology™, CSTi™ (Cancellous-Structured Titanium™) or fiber metal, for example. Trabecular Metal Technology™, CSTi™, and Cancellous-Structured Titanium™ are trademarks of Zimmer Technology, Inc of Warsaw, Ind. By facilitating bone ingrowth, additional strength and rigidity may be provided to modular prostheses 8, 60, 70, 80, 90. Additionally, bodies 11, 13 of neck 10 and anchor 12, respectively, may be formed entirely of a material made using Trabecular Metal Technology™, CSTi™, or fiber metal, for example.

As described and depicted herein, head end 14 of neck 10 includes tapered surface 24. Tapered surface 24 may be configured to accept a prosthetic component, such as a traditional metallic femoral head (not shown), with an internal female 12/14 taper, for example. Thus, once modular prosthesis 8 is implanted, as described in detail above, the additional prosthetic component, may be connected to head end 14 of neck 10. Additionally, tapered surface 24 and head end 14 may be curved to promote a more secure locking engagement and to potentially lessen third body wear debris. Although described and depicted as having tapered surface 24, head end 14 may lack tapered surface 24 and, instead, be, e.g., laser welded, electron beam welded, ultrasonically welded, glued, epoxied, cold welded, bent, deformed, screwed, bolted, or pinned to a corresponding head component.

Figure 21:
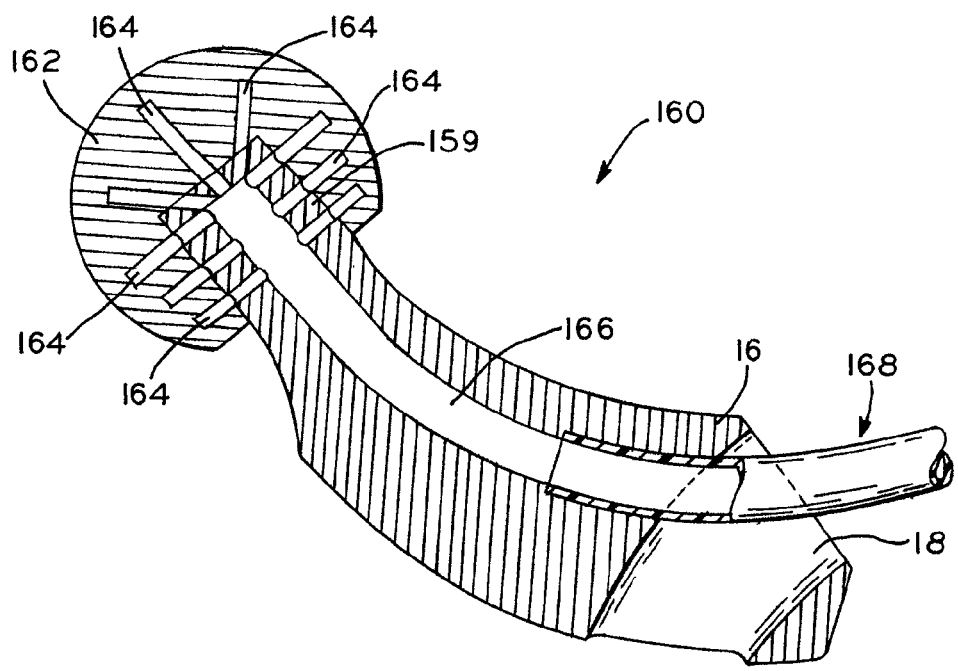
FIG. 21 is a fragmentary cross-sectional view of a component of the modular prosthesis according to another embodiment of the present invention.
Figure 22:
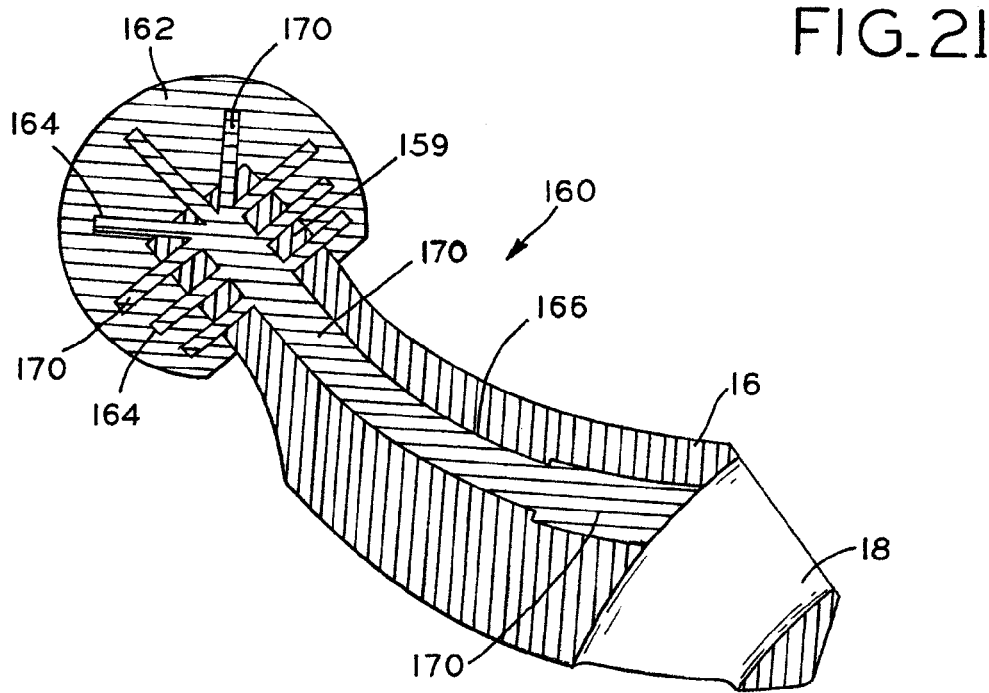
FIG. 22 is a fragmentary cross-sectional view of the component of FIG. 21 depicting biocompatible material positioned therein.

In one exemplary embodiment, shown in FIGS. 21 and 22, neck 160 may be used in conjunction with any of the anchors described herein and may be modified to incorporate any of the geometries or other features of the necks described herein. Referring to FIGS. 21 and 22, neck 160 includes several features that are identical or substantially identical to corresponding features of neck 10 and identical reference numerals have been used to identify identical or substantially identical features therebetween. Positioned on head end 159 of neck 160 is deformable head 162. In one exemplary embodiment, deformable head 162 includes a plurality of channels 164 formed therein in fluid communication with passageway 166 extending from connection end 16 of neck 160 and in fluid communication with aperture 18. Sized for receipt within a portion of passageway 166 is cannula 168. Cannula 168 is configured to allow for the passage of a biocompatible, injectable material, such as bone cement.

To expand deformable head 162 and rigidly fix the same, a biocompatible material in injected through cannula 168 and forced into passageway 166 and into channels 164 of deformable head 162. The receipt of biocompatible material causes deformable head 162 to expend from a retracted state (not shown) to the expanded state shown in FIGS. 21 and 22. In one exemplary embodiment, deformable head 162 is formed as a balloon that is deflated for passage through a lateral incision, such as those described in detail above, and is then inflated into a final, expanded position by the receipt of biocompatible material. In another exemplary embodiment, deformable head 162 is formed of a resiliently deformable material that may be compressed for passage through a lateral incision. Once deformable head 162 is filled with biocompatible material, such as bone cement 170 (FIG. 22), the biocompatible material is allowed to cure, such as by exposure to infrared light or the passage of time, to rigidly fix deformable head 162 in the expanded position.

In one exemplary embodiment, deformable head 162 may be formed from a hydrogel, calcium phosphate, or an injectable polymer, such as urethane, for example. In another ememplary embodiment, deformable head 162 may be formed from a shape-memory metal that would allow for sufficient deformation for deformable head 162 to pass through passageway 166, such as Nitinol. In another exemplary embodiment, the outer surface of deformable head 162 may be formed from a resorbable fabric, mesh, and/or sheet that is capable of retaining the injected biocompatible material, such as bone cement 170 (FIG. 22). In this embodiment, the resorbable fabric, mesh, and/or sheet retains the injected biocompatible material until it form a substantially solid compound by drying, curing, and/or polymerizing, for example. In another exemplary embodiment, a woven material may be used in conjunction with a biocompatible material to form deformable head 162 to increase the overall tensile strength of deformable head 162. For example, a titanium or tantalum fiber may be interwoven polyetheretherketone ("PEEK"), polyvinyl acetate, and/or polyvinyl pyrrolidone, for example, to achieve a desired mix of strength and loading characteristics.

Advantageously, the use of deformable head 162 eliminates the need to expose the joint capsule to insert or attach a femoral head to a femoral prosthesis. Additionally, deformable head 162 may be used in low demand applications, i.e., applications in which the patient is unlikely to place high, consistent stresses on deformable head 162, such as when the patient is elderly. By using deformable head 162, the recovery time for the patient is lessened and the amount of tissue resected decreased.

While this invention has been described as having a preferred design, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A modular prosthesis configured for receipt within a portion of a long bone, the modular prosthesis comprising:
   a prosthetic head having an articular surface, said articular surface comprising a replacement ball prosthesis for a ball-and-socket joint;
   a curved neck including an elongate body having an anatomically curved longitudinal axis, said body sized to extend through the long bone from a lateral aspect of the long bone to a head of the long bone, said body having a pair of opposing sides cooperating to define a first taper angle therebetween, said opposing sides tapered toward one another in a direction transverse to said longitudinal axis of said body along a substantial length of said elongate body, whereby said opposing sides form a wedge transverse to said longitudinal axis, said wedge having a wedge height and a wedge width, said wedge height greater than said wedge width, said neck including a connector to couple said neck to said prosthetic head; and
   an anchor including an elongate body having a longitudinal axis and a bone contacting end, said anchor curved along said longitudinal axis, said anchor sized to extend through the lateral aspect of the long bone and substantially along an anatomical axis of the long bone such that said bone contacting end of said anchor abuts a cortical bone layer of the long bone, wherein one of said neck and said anchor includes an aperture extending therethrough, said aperture extending substantially transverse to said longitudinal axis of said one of said neck and said anchor, and the other of said neck and said anchor is sized for receipt within said aperture.

2. The modular prosthesis of claim 1, wherein said neck includes said aperture extending therethrough, said aperture extending substantially transverse to said longitudinal axis of said neck, said anchor sized for receipt within said aperture.

3. The modular prosthesis of claim 2, wherein said aperture comprises a tapered aperture, whereby receipt of said anchor within said aperture forms a taper lock.

4. The modular prosthesis of claim 1, wherein at least one of said elongate body of said neck along at least of portion of said longitudinal axis of said neck and said elongate body of said anchor along at least a portion of said longitudinal axis of said anchor is tapered.

5. The modular prosthesis of claim 1, wherein at least one of said elongate body of said neck along at least of portion of said longitudinal axis of said neck and said elongate body of said anchor along at least a portion of said longitudinal axis of said anchor is tapered in a plurality of directions.

6. The modular prosthesis of claim 1, wherein said elongate body of said neck tapers in at least one direction along at least a portion of said longitudinal axis of said neck and said elongate body of said anchor tapers in at least one direction along at least a portion of said longitudinal axis of said anchor.

7. The modular prosthesis of claim 1, wherein said body of said neck includes a head end, said head end comprising said connector, said connector comprising a male tapered surface configured for attachment to said prosthetic head.

8. The modular prosthesis of claim 1, wherein said longitudinal axis of said elongate body of said neck has an anatomic curvature substantially similar to a curvature of a proximal end of the long bone.

9. The modular prosthesis of claim 8, wherein the long bone comprises a femur, wherein said anatomic curvature of said longitudinal axis is substantially similar to the curvature of a proximal end of the femur from a lateral aspect of the femur to a head of the femur, and wherein the ball-and-socket joint comprises a hip joint.

10. The modular prosthesis of claim 1, wherein said bone contacting end of said anchor is configured to abut the cortical bone layer on a lateral side of the long bone.

11. The modular prosthesis of claim 10, wherein said bone contacting end of said anchor further comprises a wall having an arcuate shape configured to substantially match a shape of the cortical bone layer, wherein said wall maximizes contact between said bone contacting end and the cortical bone layer.

12. The modular prosthesis of claim 1, wherein a portion of said elongate body of said anchor is configured to abut the cortical bone layer of the long bone on a medial side of the long bone.

13. The modular prosthesis of claim 1, wherein said connector further comprises a head end of the neck, wherein said neck is configured to abut a cortical bone layer of the long bone proximate said head end.

14. The modular prosthesis of claim 1, wherein said first taper angle is no less than five degrees and no greater than twenty-five degrees.

15. The modular prosthesis of claim 1, wherein said first taper angle is no less than ten degrees and no greater than twenty degrees.

16. A modular prosthesis configured for receipt within a portion of a long bone, the long bone having an articulating head, the modular prosthesis comprising:
   a prosthetic head having an articular surface, said articular surface comprising a replacement ball prosthesis for a ball-and-socket joint;
   a curved neck including an elongate body having an anatomically curved longitudinal axis, and connection means for securing said neck within the long bone, said body sized to extend through the long bone from a lateral aspect of the long bone to a head of the long bone, said body having a pair of opposing sides cooperating to define a first taper angle therebetween, said opposing sides tapered toward one another in a direction transverse to said longitudinal axis of said body along a substantial length of said elongate body, whereby said opposing sides form a wedge transverse to said longitudinal axis, said wedge having a wedge height and a wedge width, said wedge height greater than said wedge width, said neck including a connector to couple said neck to said prosthetic head; and
   anchor means for anchoring said neck to the long bone when said anchor means is engaged with said connection means, said anchor means sized to extend through the lateral aspect of the long bone and into an intramedullary canal of the long bone such that a portion of said anchor means abuts a cortical bone layer of the long bone, said anchor means having a longitudinal axis, said anchor means curved along said longitudinal axis.

17. The modular prosthesis of claim 16, wherein said connection means includes an aperture extending through said elongate body, said aperture formed by a tapered wall.

18. The modular prosthesis of claim 17, wherein said anchor means includes an elongate body having an outer tapered surface configured to engage said tapered surface of said aperture extending through said elongate body.

19. The modular prosthesis of claim 16, wherein said anchor means includes an elongate body having a varying radius.

20. The modular prosthesis of claim 16, wherein said connection means is transverse to the longitudinal axis of said body.

21. The modular prosthesis of claim 16, wherein said anchoring means comprises an anchor having a bone contacting end, wherein said bone contacting end is configured to abut the cortical bone layer on a lateral side of the long bone.

22. The modular prosthesis of claim 16, wherein said neck further comprises a head end, said head end comprising said connector wherein said neck is configured to abut the cortical bone layer of the long bone proximate said head end.

23. The modular prosthesis of claim 16, wherein said first taper angle is no less than five degrees and no greater than twenty-five degrees.

24. The modular prosthesis of claim 16, wherein said first taper angle is no less than ten degrees and no greater than twenty degrees.

25. A modular prosthesis configured for receipt within a portion of a long bone, the modular prosthesis comprising:
   a prosthetic head having an articular surface, said articular surface comprising a replacement ball prosthesis for a ball-and-socket joint;
   a curved neck including an elongate body having an anatomically curved longitudinal axis, a head end, and an opposing connection end, said body sized to extend through the long bone from a lateral aspect of the long bone to a head of the long bone, said body having a pair of opposing sides cooperating to define a first taper angle therebetween, said opposing sides tapered toward one another in a direction transverse to said longitudinal axis of said body along a substantial length of said elongate body, whereby said opposing sides form a wedge transverse to said longitudinal axis, said wedge having a wedge height and a wedge width, said wedge height greater than said wedge width, said neck including a connector to couple said neck to said prosthetic head; and an anchor including an elongate body having a longitudinal axis, a bone contacting end, said anchor curved along said longitudinal axis, and an opposing end, said anchor sized to extend through the lateral aspect of the long bone and substantially along an anatomical axis of the long bone such that said bone contacting end of said anchor abuts a cortical bone layer of the long bone, wherein said connection end of said neck and said opposing end of said anchor are securable to one another at a position adjacent to the lateral aspect of the long bone.

26. The modular prosthesis of claim 25, wherein said bone contacting end of said anchor is configured to abut the cortical bone layer on a lateral side of the long bone.

27. The modular prosthesis of claim 26, wherein said bone contacting end of said anchor further comprises a wall having an arcuate shape configured to substantially match a shape of the cortical bone layer, wherein said wall maximizes contact between said bone contacting end and the cortical bone layer.

28. The modular prosthesis of claim 16, wherein a portion of said elongate body of said anchor is configured to abut the cortical bone layer of the long bone on a medial side of the long bone.

29. The modular prosthesis of claim 16, wherein said neck is configured to abut the cortical bone layer of the long bone proximate said head end.

30. The modular prosthesis of claim 25, wherein said first taper angle is no less than five degrees and no greater than twenty-five degrees.

31. The modular prosthesis of claim 25, wherein said first taper angle is no less than ten degrees and no greater than twenty degrees.

* * * * *